US007889836B2

(12) United States Patent
Popescu

(10) Patent No.: US 7,889,836 B2
(45) Date of Patent: Feb. 15, 2011

(54) DEVICE AND METHOD FOR DATA TRANSFER WITH HIGH DATA RATE BETWEEN TWO PARTS MOVING RELATIVE TO ONE ANOTHER AT A SLIGHT DISTANCE

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 907 days.

(21) Appl. No.: 11/746,129

(22) Filed: May 9, 2007

(65) Prior Publication Data

US 2007/0262910 A1 Nov. 15, 2007

(30) Foreign Application Priority Data

May 9, 2006 (DE) ...................... 10 2006 021 608

(51) Int. Cl.
*A61B 6/00* (2006.01)

(52) U.S. Cl. ........................................................ 378/15

(58) Field of Classification Search ................ 378/4–20
See application file for complete search history.

(56) References Cited

U.S. PATENT DOCUMENTS

| | | | | |
|---|---|---|---|---|
| 5,140,696 | A | 8/1992 | Fox | 455/41.1 |
| 5,530,422 | A | 6/1996 | Harrison | 340/500 |
| 6,301,324 | B1 | 10/2001 | Pearson, Jr. et al. | 378/15 |
| 6,862,299 | B2 | 3/2005 | Popescu | 370/516 |
| 2004/0102162 | A1 | 5/2004 | Krumme et al. | 455/73 |
| 2006/0084859 | A1 * | 4/2006 | Johnson et al. | 600/407 |

OTHER PUBLICATIONS

"Equalizing Gigabit Copper Cable Links with the MAX3800," MAXIM Integrated Products Design Note: HFDN-10.0, Rev. 1: (2001).
"Equalizing Gigabit-per-Second Signals on Copper Media," MAXIM Integrated Products Design Note: HFDN-06.0.1, Rev. 1: (2001).

* cited by examiner

*Primary Examiner*—Courtney Thomas
(74) *Attorney, Agent, or Firm*—Schiff Hardin LLP

(57) ABSTRACT

In a device and a method for data transfer between two parts moving relative to one another while maintaining a slight distance between the parts, a transmission device with at least one transmission antenna (connected with a transmitter) and a reception device with a reception antenna (connected with a receiver are used). The transmission antenna and/or the reception antenna is/are fashioned as radio-frequency conductors and are arranged such that signals fed into the transmission antenna during at least one segment of the relative movement are received by the reception antenna by capacitive or inductive coupling. One or more compensation devices is/are arranged between the transmitter and the receiver. The compensation devices counteract signal distortion caused on the radio-frequency conductor by propagation of the signals. Higher data transfer rates can be realized in a cost-effective manner given the use of radio-frequency strip conductors as transmission and/or reception antennas.

24 Claims, 4 Drawing Sheets

DEVICE AND METHOD FOR DATA TRANSFER WITH HIGH DATA RATE BETWEEN TWO PARTS MOVING RELATIVE TO ONE ANOTHER AT A SLIGHT DISTANCE

BACKGROUND OF THE INVENTION

1. Field of the Invention

The present invention concerns a device as well as a method for data transfer between two parts moving relative to one another while maintaining a slight distance between the parts.

2. Description of the Prior Art

A device of the above type is known that has a transmission device with at least one transmission antenna (connected with a transmitter) on one of the parts moving relative to one another and one receiver device that has at least one reception antenna (connected with a receiver) on the other of the parts moving relative to one another. The transmission antenna and/or the receiver antenna is/are fashioned and arranged as radio-frequency conductors, such that during at least one segment of the relative movement, signals submitted by the transmission antenna are received by the reception antenna by capacitive or inductive coupling.

The preferred application field of the present invention concerns data transfer between the rotating part and the stationary part of a computed tomography apparatus. In operation of the computed tomography apparatus the data acquired by the x-ray detectors must be transferred from the rotating part to the stationary part of the computed tomography apparatus in order to further process the data. The data quantity to be transferred increases with the continuous development of computed tomography systems.

In many presently available computed tomography apparatuses a slip ring system as known is, for example, from U.S. Pat. No. 5,140,696 or U.S. Pat. No. 5,530,422 is used for data transfer. This data transfer system has a transmission device on the rotating part as well as a reception device on the stationary part. The transmission device has at least one radio-frequency conductor connected with a transmitter and forming a transmission antenna that is arranged on the periphery of the rotating part of the rotating frame. The reception device has a receiver and at least one reception antenna connected with the receiver, this reception antenna being formed by a short segment of a radio-frequency conductor. In operation of the computed tomography apparatus, the transmission antenna moves past the reception antenna attached on the stationary part at a slight distance, such that the signals propagating on the transmitting radio-frequency conductor are capacitively launched or injected into the reception antenna via the developing wave. The radio-frequency conductors are normally fashioned as microstrip conductors in a PCB (printed circuit board) technique and can be realized cost-effectively.

This transfer technology, however, due to the steadily increasing data rate (already at multiple gigabits/s (Gbps)) in computed tomography systems, in particular in multi-line computed tomography systems, will lead to problems in the near future since the signals or data to be transferred must be conducted over a larger distance in the transmitting radio-frequency conductor dependent on the current position of the rotating frame. Given increased data rate, strong signal distortions that limit the transferable data rate arise in the data transfer due to frequency-dependent losses, in particular due to dielectric losses and the skin effect. Since a shortening of the radio-frequency conductor used in the transmission device is not possible in computed tomography systems, a higher data rate can be achieved only by the use of special low-loss dielectric materials in the radio-frequency conductor. Such materials are expensive and are not always available for the desired data rates.

SUMMARY OF THE INVENTION

An object of the present invention is to provide a device as well as a method for data transfer between two parts that are moving relative to one another while maintaining a slight distance, in particular between the rotating part and the stationary part of a computed tomography apparatus, which can be realized in an economic manner and enable a higher transferable data rate than the data transfer systems described above.

The object is achieved in accordance with the invention by a device and a method using, in a known manner, a transmission device that has at least one transmission antenna (connected with a transmitter) on one of the parts moving relative to one another and a reception device that has at least one reception antenna (connected with a receiver) on the other of the parts moving relative to one another. The transmission antenna and/or the reception antenna are each fashioned as a radio-frequency conductor and are arranged such that signals emitted by the transmission antenna during at least one segment of the relative movement are received by the reception antenna via capacitive or inductive coupling. The radio-frequency conductor can be a microstrip conductor or a waveguide. For example, the transmission antenna can be a strip conductor that extends over the entire distance of the relative movement, with the reception antenna being formed only by a short piece of a strip conductor. In accordance with the invention, one or more compensation devices is/are arranged between the transmitter and the receiver, the compensation devices counteracting signal distortion caused on the radio-frequency conductor by propagation of the signals. The one or more compensation devices thus effect a frequency-dependent increase or decrease of frequency amplitudes of the transferred signals that counteracts the frequency characteristic of the frequency-dependent attenuation caused by the signal propagation on the radio-frequency conductor, and thus at least approximately compensates this frequency-dependent attenuation.

For data rates above 1 Gbps, the signal distortion is caused primarily by dielectric losses on the radio-frequency conductor that exhibit an f−1 characteristic. The signal distortions at the receiver (as occur, for example, along with the transfer of NRZ (non-return to zero)) signals, thus can be avoided or distinctly reduced by the arrangement of suitable compensation devices for compensation of this f−1 characteristic. The device and the associated method in accordance with the invention enable the transfer of higher data rates between two parts moving relative to one another at a slight distance with data transfer systems that operate with capacitive or inductive coupling such as, for example, the slip ring systems used in computed tomography systems. The device furthermore allows the use of cost-effective materials for the radio-frequency conductor as have previously been used in computed tomography systems. The use of particularly low-loss dielectric materials, however, is naturally also possible. In this case, the present invention leads to a an even further increase of the data transfer rate at a given transfer distance.

The compensation devices can be formed by active or passive components; a combination of active and passive components is also possible. The compensation devices can be used at any point between transmitter and receiver, for example in the transmitter, in the receiver or in the radio-frequency conductor. An arrangement of a compensation device exclusively in the transmitter or exclusively in the receiver is naturally also possible.

In principle, suitable compensation devices are known from the field of radio-frequency data transfer, but these have conventionally been used with fixed transfer distances and have been exactly adapted to the length of the transfer path. In the case of data transfer between two parts moving relative to one another, however, the transfer distance changes continuously, such that the use of such components has not previously been considered for this application.

the inventive device and the associated method thus are based on the insight that a signal distortion can also be successfully countered (and thus the data transfer rate can be increased) in such an application by suitable adaptation of the compensation devices.

In one embodiment this can ensue by adaptation of the respective compensation device for the optimal compensation of a transfer distance that lies in a median range between a minimum transfer distance and a maximum transfer distance that are predetermined by the relative movement.

In another embodiment, the compensation is continuously adapted dependent on the changing transfer distance that occurs during the relative movement, in order to achieve an optimal compensation of the signal distortions for each transfer distance during the relative movement. For this purpose, the relative position between the two parts moving relative to one another is directly or indirectly detected during the relative movement (in the event that this is not already known from the controller of the relative movement) and is communicated to the one or more compensation devices. These compensation devices then alter the frequency-dependent attenuation and/or amplification of the signals continuously or in steps (advantageously by using a stored table) dependent on the relative position or the transfer distance.

In a further embodiment an active regulation of at least one of the compensation devices ensues which can be arranged, for example, in the transmitter or in the receiver). For this purpose, the energy distribution within the signals is measured at the output of the receiver in at least two frequency ranges (a high-frequency range and a low-frequency range) and is communicated to the compensation device. The compensation device then regulates the frequency-dependent amplification and/or attenuation such that an optimally uniform energy distribution within the signals in the at least two frequency ranges is obtained at the output of the receiver.

In the present device and the associated method the compensation devices can be fashioned both as passive components that attenuate the low-frequency signal portions (or at least more significantly attenuate the low-frequency signal portions than the high-frequency signal portions) or as active components that amplify the high-frequency signal portions (or at least more significantly amplify the high-frequency signal portions than the low-frequency signal portions). Given the use of active components, for example, or corresponding compensation device can be provided in the transmitter in order to effect a pre-compensation of the signal distortions, or the compensation device can be provided in the receiver in order to implement a post-compensation of the signal distortions. Suitable compensation devices can be, for example, an equalizer of the type available from the company Maxim Integrated Products, Inc.

The inventive device for data transfer is advantageously arranged in a computed tomography apparatus in which data must be transferred at high rates between the rotating part and the stationary part. The transmission antenna is advantageously fashioned as a microstrip conductor that extends around the periphery of the rotating part of the rotating frame. The reception antenna on the stationary part is advantageously a short strip conductor segment that exhibits a slight separation from the strip conductor on the rotating part of the rotating frame during the entire rotation. Variations of the transmission and reception antennas can naturally deviate from the preferred embodiment, with any design known in this context from the prior art for capacitive or inductive coupling being possible in principle.

DESCRIPTION OF THE PREFERRED EMBODIMENTS

Figure 1:
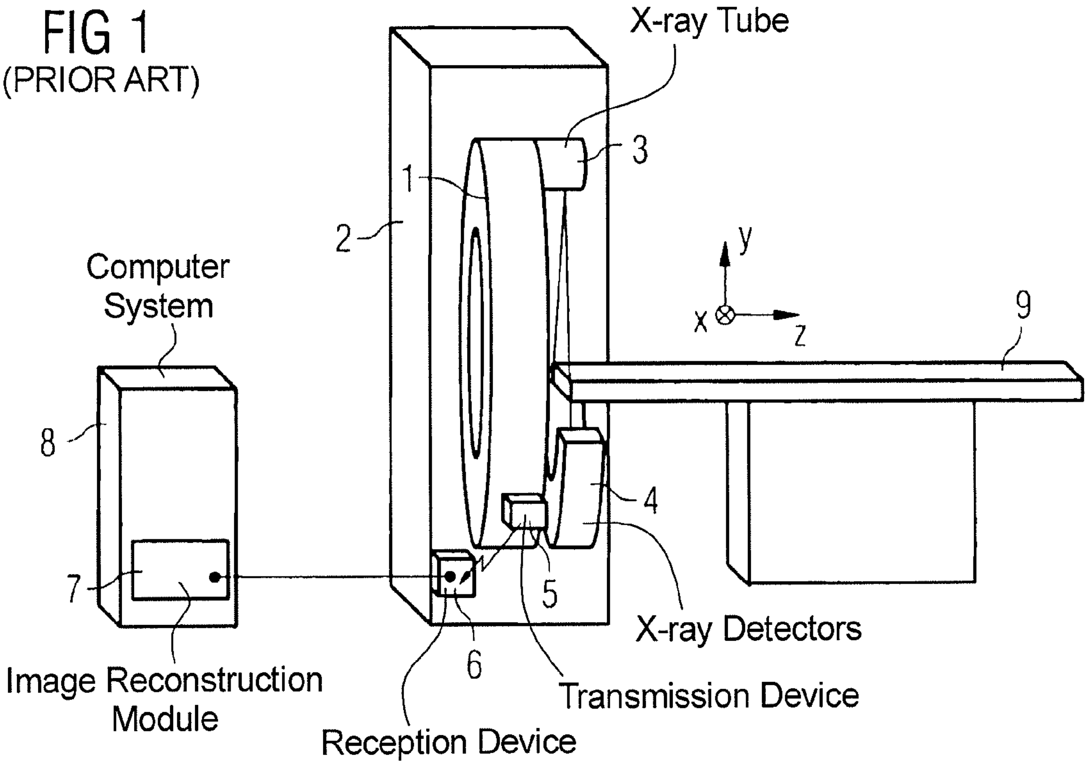
FIG 1 (PRIOR ART)
FIG. 1 is a schematic representation of a computed tomography apparatus showing the basic components of an associated data transfer system.

FIG. 1 schematically shows a computed tomography apparatus with a device for transfer of measurement data from the rotating part to the stationary part of the rotating frame. A computed tomography apparatus has, among other things, an x-ray tube 3, x-ray detectors 4 arranged in lines, and a patient positioning table 9. The x-ray tube 3 and the x-ray detectors 4 are arranged on the rotating part 1 of a rotating frame that rotates around the patient positioning table 9 and an examination axis z running parallel to this patient positioning table 9. The patient positioning table 9 normally can be displaced along the examination axis 2 relative to the rotating frame. The x-ray tube 3 generates an x-ray beam flared in a fan shape in a slice plane perpendicular to the examination axis 2. The x-ray beam, for examinations in the slice plane, penetrates a slice of a subject (for example a body slice of a patient who is on the patient positioning table 9) and strikes the x-ray detectors 4 situated opposite the x-ray tube 3. The angle at which the x-ray beam penetrates the body slice of the patient, and possibly the position of the patient positioning table 9 relative to the rotating frame 9, vary continuously during the image data acquisition with the computed tomography apparatus. During the image apparatus data acquisition the x-ray detectors 4 therefore deliver a large quantity of measurement data that must be evaluated for reconstruction of a two-dimensional slice image or a three-dimensional image of the body of the patient. The evaluation ensues in a stationary computer system 8 that is connected with the computed tomography apparatus. During the measurement data acquisition the rotating part 1 of the rotating frame rotates within the stationary part 2. The measurement data acquired by the x-ray detectors 4 are transferred with a rotating transmission device 5 (that is mounted on the rotating part 1 of the rotating frame) to a stationary reception device 6 on the stationary part 2 of the computed tomography apparatus. The data are then normally fed via an optical cable connection from the stationary reception device 6 to an image reconstruction module 7 of the computer system 8 for evaluation.

Figure 2:
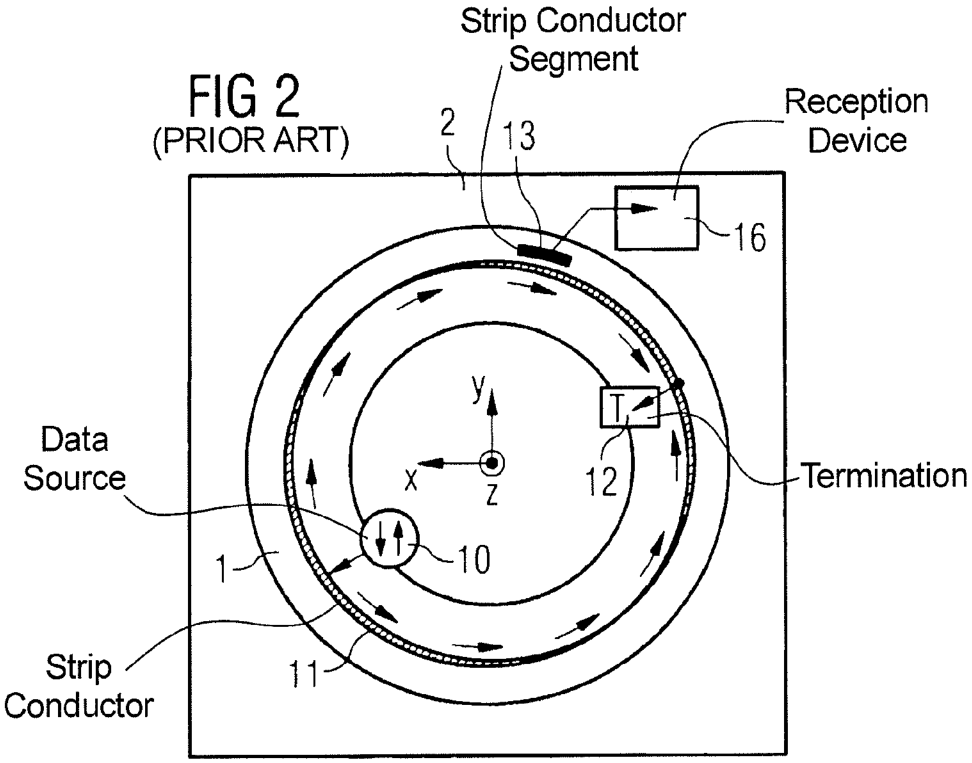
FIG 2 (PRIOR ART)
FIG. 2 shows an example for a device for data transfer in a computed tomography apparatus according to the prior art, in schematic representation.

FIG. 2 exemplarily shows an embodiment of a known data transfer device of the prior art in a schematic representation, as is used in numerous computed tomography systems. With this data transfer device the measurement data are transferred via capacitive coupling from the rotating part 1 to the stationary part 2 of the rotating frame. For this purpose, a circular RF strip conductor 11 is affixed on the rotating part 1 as a transmission antenna into which the measurement data are injected from the data source 10. The strip conductor 11 is terminated on the side situated opposite the in-feed point by a suitable impedance (termination 12). The data bits fed into the strip conductor 11 from the data source 10 propagate in both branches of the strip conductor 11 up to the termination 12. The selected splitting of the strip conductor 11 into two branches extending in opposite directions enables a continuous data transfer during the rotation of the rotating frame. The arrows in FIG. 2 show the propagation directions of the data signals in the two branches of the strip conductor 11. A short segment of an RF strip conductor 13 is arranged at the stationary part 2 of the rotating frame as a reception antenna that is part of the reception device 6 of the stationary part 2. Given rotation of the rotating part 1 of the rotating frame, the reception antenna (strip conductor 13) is located in immediate proximity to the strip conductor 11 (used as a transmission antenna) of the rotating part 1, such that the data signals fed into the strip conductor 11 are received by the reception antenna via capacitive coupling. However, at higher data rates this type of data transfer runs into problems, as explained above.

Figure 3:
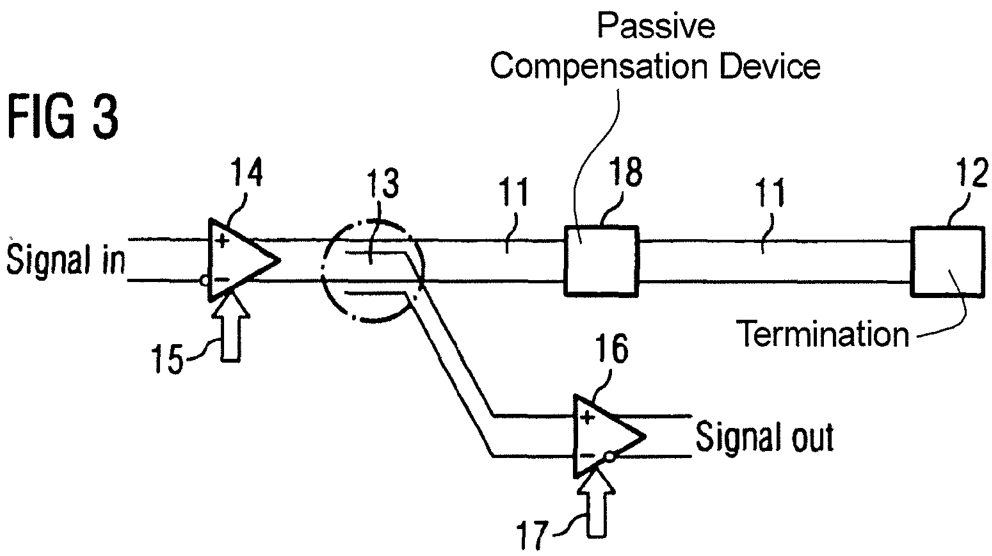
FIG. 3 shows an example for a device for data transfer according to the present invention, in schematic representation.

In the inventive device for data transfer, the basic design can be realized in the same manner as this is shown in the computed tomography apparatuses of FIGS. 1 and 2, but with the addition of one or more compensation devices. This is shown in FIG. 3, which shows the transmission device 5 and the reception device 6 according to the present invention. The transmission device 5 has a transmitter 14 that feeds an incoming signal into the strip conductor 11 serving as a transmission antenna, this strip conductor 11 being terminated with a termination 12. In the present example a first compensation device 15 is fashioned in the transmitter 14, this first compensation device 15 being indicated only by the arrow in FIG. 3. The reception device 6 is formed by a segment of a strip conductor 13 as well as a receiver 16 that, in the present example, has a compensation device 17 for post-compensation, this compensation device 17 likewise being indicated by an arrow. In the transmitter 14 the incoming signals are modulated on a carrier frequency by suitable modulation circuitry. In the receiver 16, the incoming signals are extracted again from the received signal by suitable demodulation circuitry. The signals are transferred by capacitive coupling between the two strip conductors 11, 13, which are symmetrical transfer conductors.

In the embodiment of FIG. 3 a passive compensation device 18 is also exemplarily indicated on the strip conductor 11. This passive compensation device, in the form of a passive equalizer, represents a high-pass RLC filter with a frequency response that is complementary to the frequency-dependent loss of the strip conductor 11 and thus counteracts a signal distortion caused by this frequency-dependent loss. Naturally a number of such passive compensation devices can be provided on the strip conductor 11 or 13 or also in the transmitter 14 or in the receiver 16. Such passive equalizers, however, lead to an additional loss of signal amplitude, such that in principle active compensation devices as are explained in detail in the following are preferable.

Figure 4:
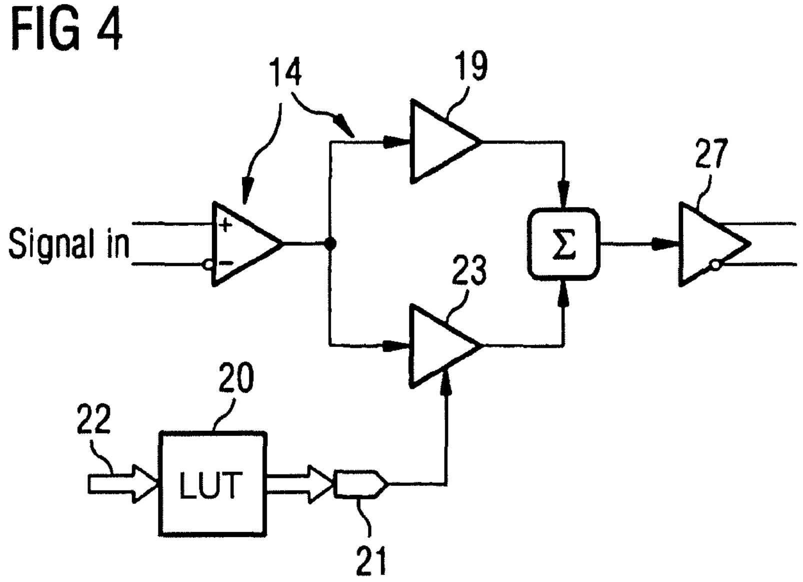
FIG. 4 shows an example for a compensation device according to the present invention in the transmitter.

FIG. 4 shows an example of such an active compensation device for pre-compensation in the transmitter 14. With this compensation device 15 for pre-compensation (pre-emphasis), the high-frequency components of the signal are amplified before they are fed into the strip conductor 11. However, the pre-compensation must be specially adapted since the transfer distance over the strip conductor 11 is not constant during the operation of a computed tomography apparatus. During the rotation of the rotating frame, the distance over which the signal propagates on the strip conductor 11 before it launches into the reception antenna depends on the current angle offset between the rotating part and the stationary part of the rotating frame. The distance is shortest for an angle offset of 0 degrees, at which the receiver 16 and the transmitter 14 lie directly opposite one another, and longest for an angle offset of 180°. An optimal pre-compensation for an angle offset of 180° would lead to a widely exaggerated pre-compensation for an angle offset of 0°. Such an exaggerated pre-compensation likewise leads to a worsening of the signal quality and causes a jitter that is not acceptable in terms of level. Different ways can be proposed to avoid this problem.

For example, a constant pre-compensation can be set at the compensation device 15 that is designed for an average transfer distance between the minimum transfer distance (at an angle offset of 0°) and the maximum transfer distance (at an angle offset of 180°). In the range of this average transfer distance the pre-compensation is set such that an optimally small deterministic jitter is achieved for angle offset of 0° and an optimally good pre-compensation is achieved for an angle offset of 180°. An optimal compensation of the signal distortions is thereby only achieved at a very transfer distance in this median range.

For further minimization of the jitter, additional devices for clock regeneration as are known from U.S. Pat. No. 6,862,299 can be used in this embodiment, as well as in other embodiments of the present device.

A second possibility of the use of the compensation device 15 for pre-compensation is to vary the compensation in real time dependent on the changing transfer distance. Given use in a computed tomography apparatus, the level of the pre-compensation is thus varied dependent on the current angle offset between the transmitter 14 and the receiver 16 in order to achieve an optimal compensation of the signal distortion for each transfer distance. The respective current relative position, i.e. the angle offset between the rotating part and the stationary part of a computed tomography apparatus, is already available both at the stationary part and at the rotating part during operation of the computed tomography apparatus, since this information is also required for the later image reconstruction. In the present embodiment this information is also provided to the compensation device 15, which then varies the level of the pre-compensation corresponding to the current angle position. The adaptation of the pre-compensation to the angle offset can be read from a table in which the different level the pre-compensation dependent on the angle offset is specified.

Figure 5:
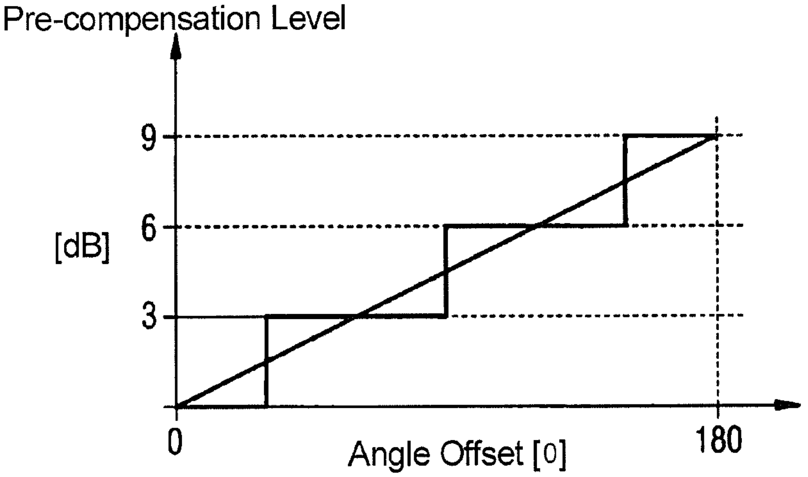
FIG. 5 illustrates two examples for a variable adaptation of the compensation dependent on the transfer distance.

FIG. 5 shows such a dependency using two examples. In the first example the level of the pre-compensation is continuously adapted with the angle offset, while a stepped adaptation ensues in the second example. This information required for the compensation device can be stored, for example, in a digital table in which the amplification coefficients dependent on the angle offset are listed. The digital coefficients are then converted via a digital/analog converter (D/A converter) into an analog control signal for controlling the amplification of the signals.

FIG. 4 shows a compensation device designed in this manner in the transmitter 14 of the present device. The compensation device includes, among other things, a linear amplifier 19 and an HF boost amplifier 23 for frequency-dependent amplification that receives the information about the level of the pre-compensation via a LUT (look-up table) 20 with a downstream D/A converter 21 dependent on the current angle offset 22 between rotating part and stationary part of the rotating frame. The pre-compensated signal is then available at the output of the transmitter 14 to be fed into the strip conductor 11.

Figure 6:
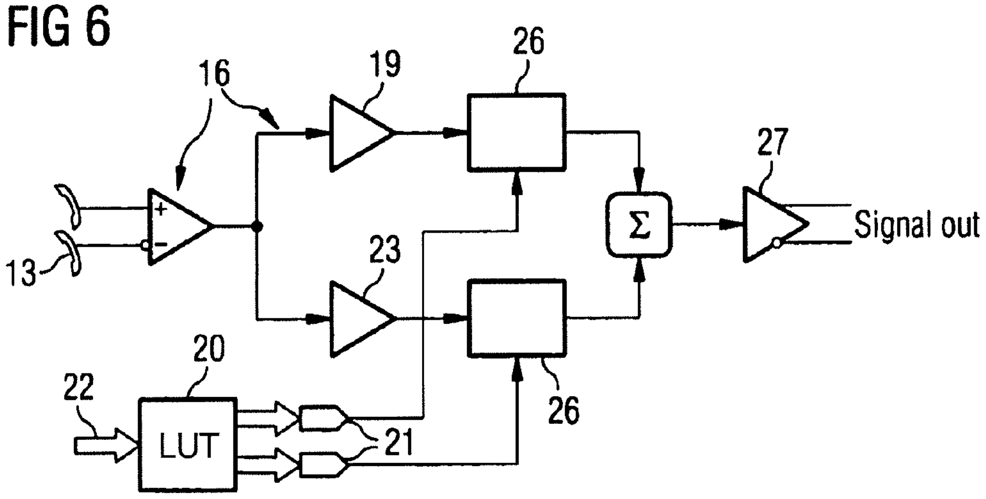
FIG. 6 shows an example for a compensation device according to the present invention in the receiver.
Figure 7:
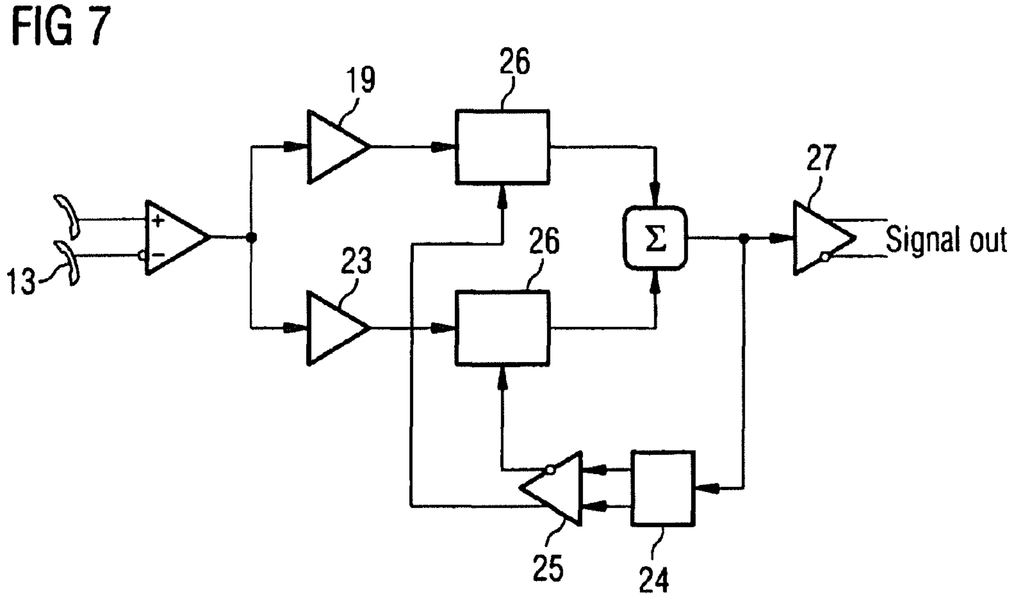
FIG. 7 shows a further example for an embodiment of a compensation device according to the present invention in the receiver.

A compensation device 17 for post-compensation in the receiver 16 can be used in the same manner, as is exemplarily shown in FIGS. 6 and 7. In this case high-frequency signal components are also more strongly amplified by the compensation device 17 (here in the embodiment of an equalizer) than low-frequency signal components, in order to compensate the frequency-dependent attenuation of the signals due to the propagation on the strip conductor 11. The continuously changing transfer distance can be considered in the same manner as was explained in connection with the compensation device 15 for pre-compensation in the transmitter.

FIG. 6 exemplarily shows a corresponding design of the compensation device 17 using an LUT 20, but in this case the frequency-dependent amplification is not varied in the RF boost amplifier 23. Rather, the amplified signals are attenuated in frequency-dependent manner by two variable attenuation elements 26, dependent on the current angle offset 22 between the rotating part and the stationary part. An output signal compensated with regard to the signal distortion is then available at the output of the receiver 16 after a limit amplifier 27 (also shown in FIG. 4). Other components in FIG. 6 correspond to those described in connection with FIGS. 3 and 4.

A further possibility of the adaptation of the post-compensation to the continuously changing transfer distance is the realization of an adaptive compensation, as is exemplarily shown in FIG. 7. In this example the energy distribution within the signal spectrum is measured at the output of the receiver 16 with two bandpass filters 24. An analog computer 25 determines the ratio of the energy between the high-frequency and low-frequency signal portions and regulates the compensation device 17 with the two variable attenuation elements 26 such that an optimally uniform distribution of the energy at the high-frequency and low-frequency signal components results at the output. An automatic adaptation of the compensation in the receiver 17 to the changing transfer distance thus ensues via the shown regulatory loop.

Such a regulation can also be realized for the pre-compensation by the analog computer 25 regulating the compensation device 15 for pre-compensation dependent on the energy distribution at the output of the receiver.

Although modifications and changes may be suggested by those skilled in the art, it is the intention of the inventor to embody within the patent warranted hereon all changes and modifications as reasonably and properly come within the scope of his contribution to the art.

The invention claimed is:

1. A device for data transfer between two parts that are moving relative to one another while maintaining a slight distance between the two parts, comprising:

a transmission device mounted on a first of said parts moving relative to one another, said transmission device comprising at least one transmission antenna connected to a signal transmitter;

a reception device mounted on a second of said parts moving relative to one another, said reception device comprising at least one reception antenna connected with a signal receiver;

at least one of said transmission antenna and said reception antenna being formed as a radio-frequency conductor and being arranged to cause signals fed into the transmission antenna from the signal transmitter to radiate from and be received by the reception antenna, via a non-galvanic transmission path, during at least one segment of the relative movement between the first and second moving parts, by capacitive coupling or inductive coupling across said non-galvanic transmission path; and at least one compensation device disposed between the signal transmitter and the signal receiver, said at least one compensation device counteracting signal distortion that occurs on said radio-frequency conductor due to propagation of said signal in said radio-frequency conductor.

2. A device as claimed in claim 1 wherein said at least one compensation device is a passive compensation device that attenuates low-frequency signal components of said signal relative to higher-frequency signal components of said signal.

3. A device as claimed in claim 2 wherein said passive compensation device is a filter having a filter characteristic that compensates a frequency dependency of the signal attenuation that occurs at a signal transfer distance between said signal transmitter and said signal receiver during propagation of said signal in said radio-frequency conductor.

4. A device as claimed in claim 1 wherein said at least one compensation device is an active compensation device that frequency-dependently amplifies said signal to more strongly amplify higher-frequency signal components of said signal relative to lower-frequency components of said signal.

5. A device as claimed in claim 4 wherein said active compensation device comprises an input that receives an input signal indicative of a current signal transfer distance between said signal transmitter and said signal receiver, said active compensation device changing the frequency-dependent amplification also dependent on said signal transfer distance to counteract said signal distortion at each signal transfer distance that occurs during movement of said first and second moving parts.

6. A device as claimed in claim 5 wherein said active compensation device comprises a memory containing a table from which said active compensation device reads respective frequency-dependent amplifications for different signal transfer distances.

7. A device as claimed in claim 4 comprising a measurement device that measures an energy distribution of low-frequency components and high-frequency components of an output signal of said signal receiver, and comprising a regulatory loop in which said active compensation device and said measurement device are connected, with said active compensation device regulating the frequency-dependent amplification, dependent on said energy distribution, to produce a uniform energy distribution at said output of said signal receiver.

8. A device as claimed in claim 4 wherein said active compensation device frequency-dependently amplifies said signal to at least approximately compensate a frequency dependency of the signal attenuation of said signal propagating in said radio-frequency conductor, at a signal transfer distance between said signal transmitter and said signal receiver.

9. A device as claimed in claim 1 wherein said at least one compensation device counteracts said signal distortion for a signal transfer distance between said signal transmitter and said signal receiver that is in a median range between a maximum signal transfer distance and a minimum signal transfer distance caused by said relative movement of said first and second moving parts.

10. A device as claimed in claim 1 wherein said at least one compensation device counteracts said signal distortion for a signal transfer distance between said signal transmitter and said signal receiver that is in a median range between a maximum distance and a minimum distance caused by the relative movement of the first and second parts, to produce a minimum jitter at said minimum distance.

11. A device as claimed in claim 1 wherein said radio-frequency conductor is a strip conductor.

12. A device as claimed in claim 1 wherein said first and second moving parts are respectively a rotating part and a stationary part of a computed tomography apparatus.

13. A method for data transfer between two parts that are moving relative to one another while maintaining a slight distance between the two parts, said method comprising the steps of:

transmitting signals by radiation via a non-galvanic transmission path using a transmission device mounted on a first of said parts moving relative to one another, said transmission device comprising at least one transmission antenna connected to a signal transmitter;

receiving the transmitted signals using a reception device mounted on a second of said parts moving relative to one another, said reception device comprising at least one reception antenna connected with a signal receiver, at least one of said transmission antenna and said reception antenna being formed as a radio-frequency conductor;

arranging said transmission antenna and said reception antenna respectively on said parts to cause signals fed into the transmission antenna from the signal transmitter to be received by the reception antenna via said non-galvanic transmission path during at least one segment of the relative movement between the first and second moving parts, by capacitive coupling or inductive coupling across said non-galvanic transmission path; and disposing at least one compensation device disposed between the signal transmitter and the signal receiver, and with said at least one compensation device, counteracting signal distortion that occurs on said radio-frequency conductor due to propagation of said signal in said radio-frequency conductor.

14. A method as claimed in claim 13 comprising employing a passive compensation device as said at least one compensation device that attenuates low-frequency signal components of said signal relative to higher-frequency signal components of said signal.

15. A method as claimed in claim 14 comprising, with said passive compensation device, filtering said signal with a filter having a filter characteristic that compensates a frequency dependency of the signal attenuation that occurs at a signal transfer distance between said signal transmitter and said signal receiver during propagation of said signal in said radio-frequency conductor.

16. A method as claimed in claim 13 comprising employing an active compensation device as said at least one compensation device that frequency-dependently amplifies said signal to more strongly amplify higher-frequency signal components of said signal relative to lower-frequency components of said signal.

17. A method as claimed in claim 16 comprising providing an input signal to said active compensation device indicative of a current signal transfer distance between said signal transmitter and said signal receiver, and with said active compensation device, changing the frequency-dependent amplification also dependent on said signal transfer distance to counteract said signal distortion at each transfer distance that occurs during movement of said first and second moving parts.

18. A method as claimed in claim 17 comprising providing said active compensation device with access to a memory containing a table from which said active compensation device reads respective frequency-dependent amplifications for different signal transfer distances.

19. A method as claimed in claim 17 comprising measuring an energy distribution of low-frequency components and high-frequency components of an output signal of said signal receiver, and comprising regulating the frequency-dependent amplification of said active compensation device, dependent on said energy distribution to produce a uniform energy distribution at said output of said signal receiver.

20. A method as claimed in claim 17 comprising with said active compensation device, frequency-dependently amplifying said signal to at least approximately compensate a frequency dependency of the signal attenuation of said signal propagating in said radio-frequency conductor, at a signal transfer distance between said signal transmitter and said signal receiver.

21. A method as claimed in claim 13 comprising with said at least one compensation device, counteracting said signal distortion for a signal transfer distance between said signal transmitter and said signal receiver that is in a median range between a maximum signal transfer distance and a minimum signal transfer distance caused by said relative movement of said first and second moving parts.

22. A method as claimed in claim 13 comprising, with said at least one compensation device counteracting said signal distortion for a signal transfer distance between said signal transmitter and said signal receiver that is in a median range between a maximum distance and a minimum distance caused by the relative movement of the first and second parts, to produce a minimum jitter at said minimum distance.

23. A method as claimed in claim 13 comprising employing a strip conductor as said radio-frequency conductor.

24. A method as claimed in claim 13 comprising employing, as said first and second moving parts, respectively, a rotating part and a stationary part of a computed tomography apparatus.

* * * * *